(12) United States Patent
Lamb et al.

(10) Patent No.: US 6,228,108 B1
(45) Date of Patent: *May 8, 2001

(54) HEAT TRANSFERRING THERAPEUTIC PACK

(75) Inventors: Steve Lamb, Union City, CA (US); Richard Emerson, Phoenix; Richard L. Rusche, Scottsdale, both of AZ (US)

(73) Assignee: Orthopedic Systems, Inc., Union City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/221,271

(22) Filed: Dec. 23, 1998

(51) Int. Cl.⁷ ........................................... A61F 7/00
(52) U.S. Cl. ..................... 607/112; 607/114; 607/108
(58) Field of Search ................. 607/108, 112, 607/109, 110, 111, 114

(56) References Cited

U.S. PATENT DOCUMENTS

| | | | |
|---|---|---|---|
| 4,081,150 | * | 3/1978 | Tyson .................... 128/402 |
| 4,517,972 | * | 5/1985 | Finch, Jr. ................ 128/156 |
| 4,586,506 | | 5/1986 | Nangle . |
| 4,706,673 | * | 11/1987 | Meistrell ................ 128/402 |
| 4,981,135 | * | 1/1991 | Hardy .................... 128/402 |
| 5,557,801 | * | 9/1996 | Jakus ......................... 2/2 |
| 5,584,086 | | 12/1996 | VanWinkle et al. . |
| 5,628,772 | | 5/1997 | Russell . |
| 5,728,147 | * | 3/1998 | Thomas ................... 607/112 |
| 5,766,235 | | 6/1998 | Kostopoulos . |
| 5,800,492 | * | 9/1998 | Manker .................. 607/111 |
| 5,823,984 | * | 10/1998 | Silverberg ............... 602/61 |

* cited by examiner

*Primary Examiner*—Lee Cohen
*Assistant Examiner*—Jocelyn Debra Ram
(74) *Attorney, Agent, or Firm*—Theodore J. Bielen, Jr.

(57) ABSTRACT

A heat transferring therapeutic pack utilizing a mass of thermal material for application to a human body in order to apply a hot or cold compress. The therapeutic pack utilizes a flexible container having an inner chamber which holds the mass of thermal material. A pair of outer surfaces in general opposition to one another surround the inner chamber. A heated material is connected to one of the outer surfaces of the flexible container and includes hook and/or pile fasteners. The second surface of the sheet of material connects to one of the outer surfaces of the flexible container. The other outer surface of the flexible container is able to directly contact the human body permitting heat transferring applications.

4 Claims, 2 Drawing Sheets

HEAT TRANSFERRING THERAPEUTIC PACK

BACKGROUND OF THE INVENTION

The present invention relates to a novel therapeutic pack which is used to transfer heat away from or to a human body.

Traumatic injuries and other maladies often require the application of heat or the removal of heat to the surface of the human body. Generally, ice packs have been employed to inhibit swelling, while the application of heat is generally intended to promote healing. The application of hot and cold packs to areas of the body are normally used to effect such treatment. In the past, heat producing or cold producing materials, i.e. thermal materials, have been placed in a bag and held to a portion of the human body by the injured person or by an attendant. Unfortunately, the act of holding such heat transfer in therapeutic packs is tedious and requires great effort over a long period of time.

In the past, devices and apparatuses have been employed to hold heat transferring packs to the body by the use of straps and pouches. For example, U.S. Pat. Nos. 4,586,506, 5,628,772, and 5,766,235 show containers which generally include a mesh covering or layer between the thermal material and the body portion to which the heat transferring pack is applied. In many cases several layers interpose the human body and the thermal material to provide protection to the human skin, but resulting in inefficient heat transfer.

U.S. Pat. No. 5,823,984 shows an expandable wrap with panels to form packets which hold hot or cold thermal packs.

U.S. Pat. No. 5,584,086 discloses a therapeutic pillow in which a thermal liquid is used inside a chamber having a number of baffles to evenly spread the transfer of heat.

A therapeutic heat transferring pack which efficiently transfers the heat to a body part would be an advance in the medical arts.

SUMMARY OF THE INVENTION

In accordance with the present invention a novel and useful heat transferring therapeutic pack is herein provided.

The heat transferring therapeutic pack of the present invention utilizes a mass of thermal material which is capable of cooling or heating an object coming into contact with the same. The pack of the present invention includes a flexible container formed with an inner chamber for holding the mass of thermal material. The container further provides an inner surface, and a pair of outer surfaces, which may be opposed to one another, if the container is collapsed to a certain degree. The first outer surface of the flexible container is intended to directly contact the human body to permit heat transfer relative to the thermal material found in the inner chamber. The flexible container may be formed of a plastic like material which is waterproof and, essentially, sealed in an air-tight fashion.

A sheet of material is also employed in the present invention to interact with the flexible container second surface. The sheet of material may be a flexible body which possesses a first surface and an opposite second surface. The second surface of the sheet of material selectively includes hook or pile fasteners. Connecting means holds the first surface of the sheet of material to the second outer surface of the flexible container. In certain embodiments, the connecting means may take the form of an adhesive layer, however, the sheet of material may be fastened by other means such as fasteners, welding, and integrally forming the same as a wall of the container. In any case, the combined flexible container and sheet of material allows the first surface of the flexible container to be free of intervening pockets and meshes to directly contact the human body. The second surface of the container, thus, presents a surface selectively having a hook or pile fastener structure, via the sheet of material connected thereto.

Fastening means is also utilized to maintain contact of the flexible container first surface with the human body. Such fastening means may be formed into a strap having the complimentary hook or pile fasteners, which would directly attach to the complementary second surface of the sheet of material. It should be noted, that the sheet of material may also be a flexible body to allow conformation of the therapeutic pack of the present invention to the contours of human body parts.

Another aspect of the present invention may be found in an embodiment which utilizes a sheet of material that substantially encloses the first and second surfaces of the flexible container. In such a case, the connecting means would hold the sheet of material to the outer surfaces of the container. Alternately, the sheet of material may itself be integrally formed as the flexible container wall thus eliminating a dual layering of a portion of the wall of the therapeutic pack of the present invention. In such an embodiment, the hook or pile fastening material would overlie the entire outer surface of the sheet of material forming the container. Preferably, such material may be the pile type fastener material to provide comfort to the user when the pack is applied to the human body. The pile material would serve to insulate any heat or cold transferring process, and may provide moisture wicking in certain cases, dependent on the type of pile material employed.

It may be apparent that a novel and useful heat transferring therapeutic pack has been herein described.

It is therefore an object of the present invention to provide a heat transferring therapeutic pack which eliminates the use of pockets, meshes, and containers to hold a thermal material against a human body.

Another object of the present invention is to provide a heat transferring therapeutic pack which does-not injure or burn the skin of the user when it is applied thereto.

Another object of the present invention is to provide a heat transferring therapeutic pack which is easy and convenient to employ and conforms to the contours of the human body.

A further object of the present invention is to provide a heat transferring therapeutic pack which is capable of directly applying a hot or cold thermal transfer to a human body and is capable of wicking moisture therefrom at the same time.

The invention possesses other objects and advantages especially as concerns particular characteristics and features thereof which will become apparent as the specification continues.

For a better understanding reference is made to the following detailed description of the preferred embodiments thereof which should be taken in conjunction with the prior described drawings.

DETAILED DESCRIPTION OF THE PREFERRED EMBODIMENTS

Various aspects of the present invention will evolve from the following detailed description of the preferred embodiments thereof, which should be referenced to the hereinbefore delineated drawings.

Figure 1:
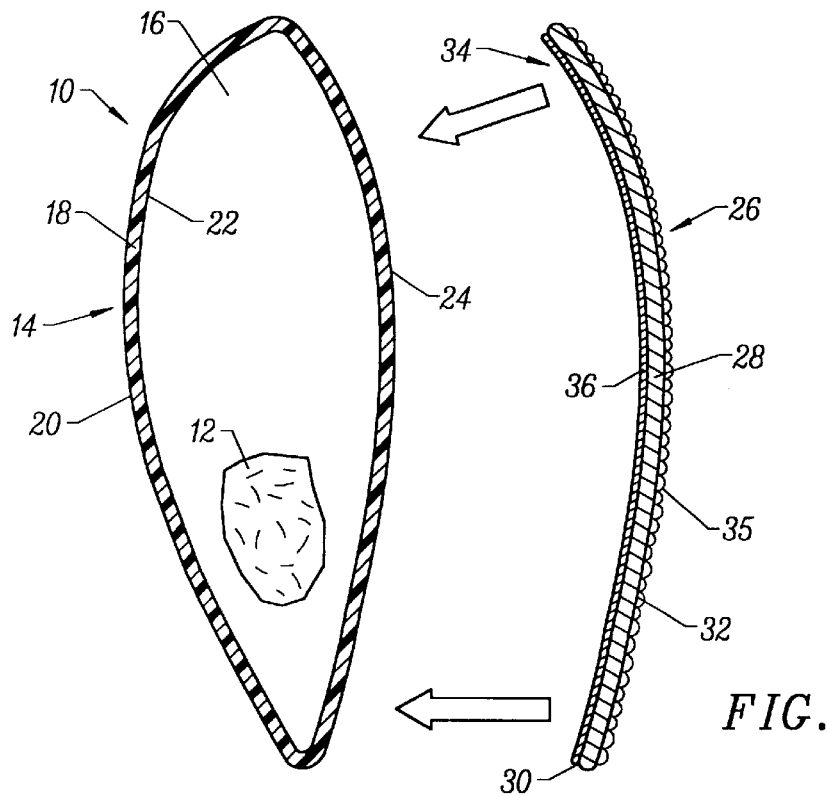
FIG. 1 is a sectional view of the therapeutic pack of the present invention with a portion of the sheet of material exploded therefrom.

The invention as a whole is shown in the drawings by reference character 10. Heat transferring therapeutic pack 10 is intended to be employed with a mass of thermal material 12, depicted in part in FIGS. 1, 2, and 4. Thermal material 12 may take the form of a heat producing material or the form of a cold producing material, as the treatment demands. In the latter situation, a product known as Power Ice manufactured by Four C Enterprises, Inc. of Phoenix, Arizona would suffice. Such material is known to be more gentle in cooling the human body than cold gels or water ice.

Thermal material 12 is sealed within a container 14 formed of a plastic or rubber like material, such as polyurethane. Container or bag 14 is necessarily moisture proof and air tight. Although thermal material 12 is depicted in part in FIG. 1, it should be understood that thermal material 12 may fill most of inner chamber 16 formed by wall 18 of container 14. Packs of the prior art consisting, merely of container 14, would be manually held to bodily parts, which has been proven to be unsuitable. Container 14 is shown partially collapsed in FIG. 1 and clearly reveals a first outer surface 20, inner surface 22, and a second outer surface 24.

Figure 2:
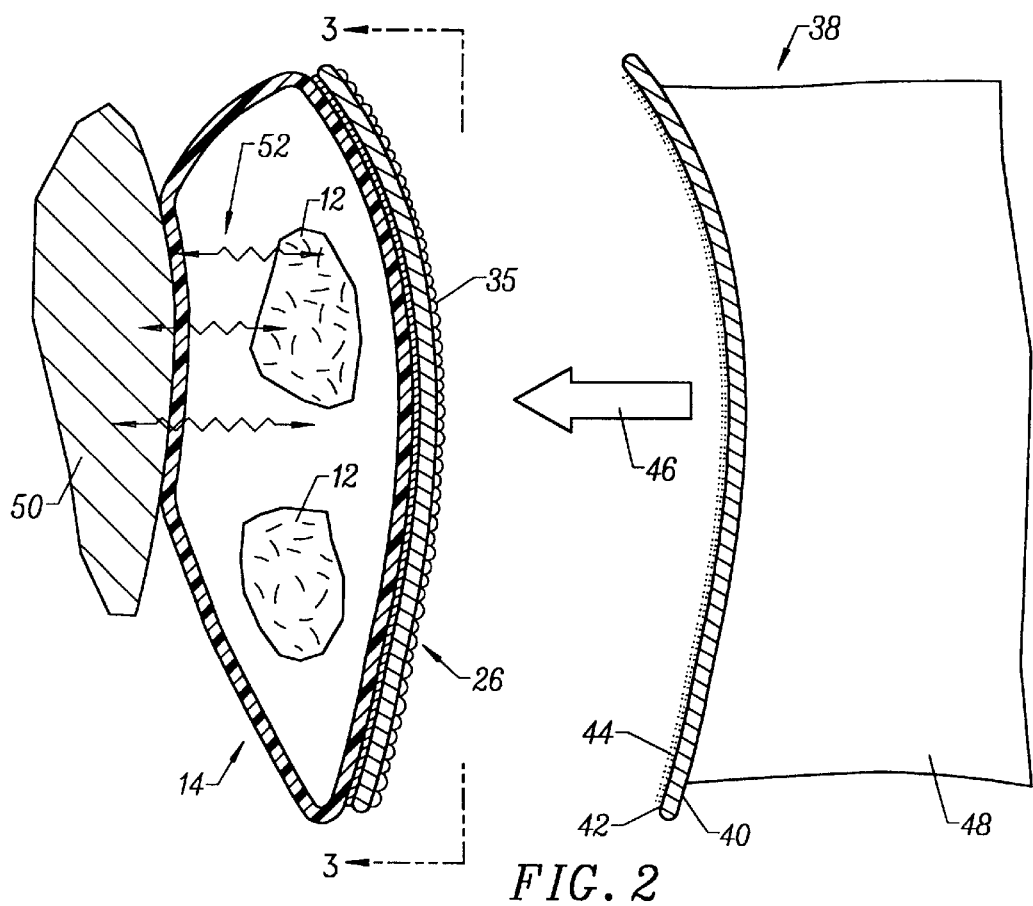
FIG. 2 is a sectional view of the therapeutic pack of the present invention in place on the body with the fastening means separated therefrom.
Figure 3:
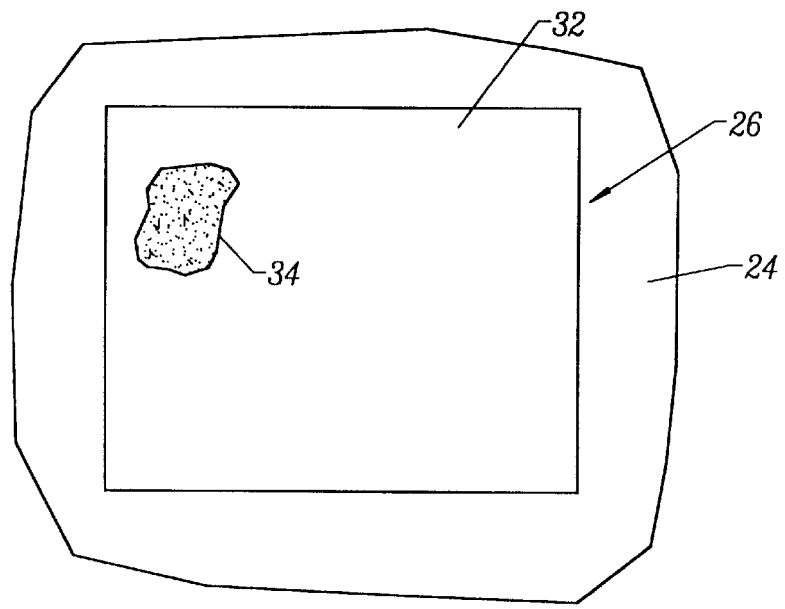
FIG. 3 is a right side view of the therapeutic pack of the present invention taken along line 3—3 of FIG. 2.

Referring again to FIG. 1, sheet of material 26 is employed in the present invention and possesses a layer 28, as well as a first surface 30 and an opposite second surface 32. Second surface 32 is formed with either hook or pile fasteners, however hook fasteners 35 are depicted in the drawings. Connecting means 34 is also utilized in the present invention to hold first surface 30 of sheet of material to second outer surface 24 of container 14. Such connecting means 34 may take the form of any known fastening entities, such as fasteners, welding, clamps, and the like. In the present embodiment, connecting means 34 is shown as a mastic layer 36. Turning to FIG. 2, it may be observed that connecting means 34 has been implemented such that sheet of material 26 is held to container 14 such that hook fasteners 35 are presented outwardly for use. In viewing FIG. 3, it may be observed that sheet of material 26 is formed into a rectangular configuration. It should be again obvious that other configurations of any type are suitable to present hook and fastening material, such as hook fasteners 35, for use.

Turning now to FIG. 2, it may be seen that fastening means 38 is illustrated. Fastening means 38 takes the form of a patch 40 with hook and/or pile material on its outer surface 42, complementary to such material on second surface 32 of sheet 26. Specifically, pile layer 44 is shown to complement the hook fasteners 35 on second surface 32 of sheet of material 26 held to container 14. Directional arrow 46 indicates the movement necessary to mate patch 40 with sheet of material 26. Strap 48, shown in part in FIG. 2, wraps around portions of the human body to hold pack 10 in place against body part 50. Plurality of heat transfer arrows 52 are intended to show that heat may travel from thermal material 12 to body part 50 or in the opposite direction through a cooling thermal material 12. In other words, thermal material 12 may be exothermic or endothermic in nature.

Figure 4:
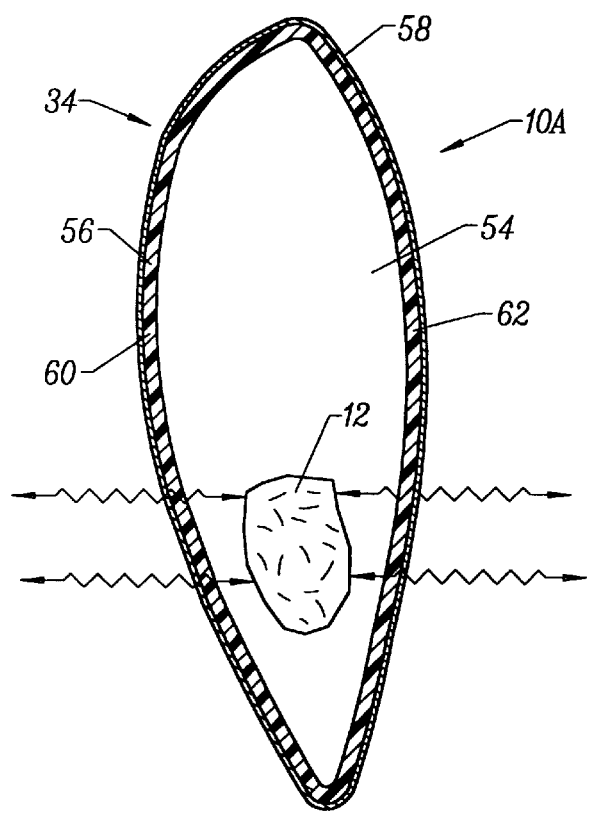
FIG. 4 is a sectional view of an alternate embodiment of the present invention.

Viewing now FIG. 4, another embodiment 10A of the present invention is depicted. Thermal material 12 is again located in a chamber 54 formed by a single wall 56 of moisture and air tight material such as polyurethane. A layer of hook and pile fastener material, such as pile material 58, extends completely around wall 56. Thus, connecting means 34 is manifested by integrally forming layer 28 of sheet of material 26 with a portion of wall 18 of container 14 of FIG. 1, specifically the portion of wall 18 having second outer surface 24. In this embodiment, thermal material 12 is free to radiate heat or emanate cold through wall 60 or wall 62. Pile material 58, when placed against body part 50 (not shown) would insulate and wick moisture from the surface of body part 50 when the pile material is composed of wicking fibers such as polypropylene.

In operation, the user places container 14 against body part 50 to permit the thermal transfer between thermal material 12 and body part 50 as shown in FIG. 2. Hook fasteners 35 are presented for use at this time. Fastening means 38 is used to hold strap 48 to container 14 by mating pile layer 44 on patch 40 to hook fasteners 35 on container 14. Straps 48 are then wrapped about other portions of the human body to press surface 20 of wall 18 against body part 50. Thermal transfer takes place from thermal material 12 to body part 50 through inner surface 22 of wall 18 and outer surface 20 of container 14. In the embodiment shown in FIG. 4, the same process takes place in which a patch having hook material is attached to any part of the outer surface 58 thereof. Again, thermal transfer takes place between thermal material 12 and a body part, such as body part 50 of FIG. 2. Pile material 58 of pack 10A serves to insulate such heat transferring process and to wick moisture from the skin surface of body part 50, in certain cases.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A heat transferring therapeutic pack utilizing a mass of thermal material for application to a human body, comprising:

a. a flexible container formed with an inner chamber for holding the mass of thermal material; said container including an inner surface contacting the thermal material, a first outer surface, and a second outer surface, said first outer surface adapted to directly contact a human body, said second outer surface adapted to remain free of contact of the human body;

b. a sheet of material, said sheet of material including a first surface and an opposite second surface, said second surface of said sheet of material selectively possessing hook and pile fasteners;

c. connecting means for holding said first surface of said sheet of material to said second outer surface of said flexible container, said connecting means further comprising integrally forming said flexible container with said sheet of material, said second surface of said sheet of material forming at least a portion of said second outer surface of said flexible container;

d. fastening means for maintaining said direct contact between said flexible container first surface and the human body, said fastening means including hook and pile fasteners complementing said hook or pile fasteners of said sheet of material, said connecting means and fastening means maintaining said direct contact between said flexible container first surface and the human body without interrupting said direct contact therebetween.

2. The heat transfer therapeutic pack of claim 1 in which said second surface of said sheet of material possesses a hook type fastener.

3. The heat transferring therapeutic pack of claim 1 in which said sheet of material is a flexible member.

4. The heat transferring pack of claim 1 in which said sheet of material forms at least a portion of said first outer surface of said flexible container.

* * * * *